United States Patent [19]

Hofmann

[11] Patent Number: 5,041,676

[45] Date of Patent: Aug. 20, 1991

[54] HIGHLY PURE ALKYL AND ARYL PHOSPHINES FOR GAS PHASE EPITAXY PROCESSES

[76] Inventor: Hartmut Hofmann, Chemetall GmbH, Reuterweg 14, D-6000 Frankfurt a. Main, Fed. Rep. of Germany

[21] Appl. No.: 451,469

[22] Filed: Dec. 15, 1989

[30] Foreign Application Priority Data

Dec. 15, 1988 [DE] Fed. Rep. of Germany ....... 3842161

[51] Int. Cl.$^5$ ................................................ C07F 9/02
[52] U.S. Cl. .......................................... 568/8; 568/17
[58] Field of Search ....................................... 568/8, 17

[56] References Cited

U.S. PATENT DOCUMENTS

| | | | |
|---|---|---|---|
| 4,246,204 | 1/1981 | Brogen | 568/17 |
| 4,299,986 | 11/1981 | Cucinella | 568/8 |
| 4,301,301 | 11/1981 | Fukui | 568/17 |
| 4,507,502 | 3/1985 | Nelson | 568/17 |
| 4,507,503 | 3/1985 | Frey et al. | 568/8 X |
| 4,507,504 | 3/1985 | Lee et al. | 568/8 X |
| 4,514,575 | 4/1985 | Lee et al. | 568/17 |

*Primary Examiner*—Paul F. Shaver
*Attorney, Agent, or Firm*—Lockwood, Alex, FitzGibbon & Cummings

[57] ABSTRACT

A process for the production of highly pure alkyl and arylphosphines for gas phase epitaxy processes through the reduction of alkyl and arylphosphinic acid or alkyl and arylphosphonic acid derivatives, with substituted alkali metal aluminum hydrides in a high-boiling solvent such as 1-methylnaphthalin.

23 Claims, No Drawings

HIGHLY PURE ALKYL AND ARYL PHOSPHINES FOR GAS PHASE EPITAXY PROCESSES

BACKGROUND AND DESCRIPTION OF THE INVENTION

The invention relates to a process for the preparation of highly pure alkyl and arylphosphines for gas phase epitaxy processes through the reduction of alkyl and arylphosphonic acid or alkyl and arylphosphinic acid derivatives.

Highly toxic gaseous phosphine is used in the electronics industry for various applications in the area of component production primarily for the doping of silicon. It has also been increasingly used recently for the production of thin connection semiconductor layers, as well as for example, GaInAsP for optical electronic purposes. The established processes such as "metal organic vapor phase epitaxy" and, most recently, "metal organic molecular beam epitaxy" have also been used in this connection. Because of the very high risk potential due to the toxicity of the phosphine and the self ignition caused by the diphosphine which is always present as a by-product, as well as the gaseous aggregate condition at room temperature, there exists the urgent necessity of describing a source of phosphorus for doping which is less dangerous and more practical in application and preparation.

In recent times, t-butylphosphine (TBP) as an organic phosphorus hydride has been recognized as a source of phosphorus doping. The difficulty of preparing this substance for that application is the fact that it could not be synthesized to sufficient purity in view of its by-products. The long known classical methods for its synthesis create problems, not only because of the expensive production processes and the low yields, but also because of the need to use starting materials which are difficult to obtain in pure form.

It is thus the task of the invention to produce highly pure alkyl and arylphosphines for the previously stated processes which can be produced in a simple reaction process in which the alkyl and arylphosphines can easily be isolated as end products in a high yield and without problems in separation.

In accordance with the invention, phosphinic and phosphonic acid derivatives, such as for example acid dihalogenides and/or esters, are used as phosphorus containing starting materials. The halogenide may be fluoride, bromide, chloride or iodide compounds. The organic parts consist of linear and/or cyclical alkyl or aryl groups, which can also be substituted. This means that the organic parts can be uniform or completely different.

The corresponding bis-analog compounds which are bonded by means of hydrocarbon bridges are additionally used, whereby all the halogenides listed above can be used as acid dihalogenides. Both linear and cyclical hydrocarbons as well as aromatic systems can function as ester radicals even in combination with one another. The analogous diphosphonic acid derivatives can also be used. Examples of such compounds include:

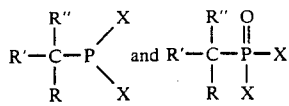

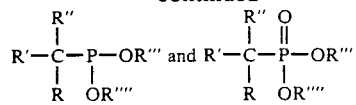

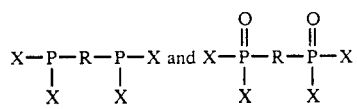

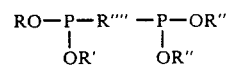

and

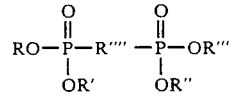

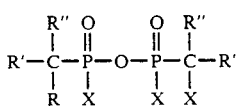

and

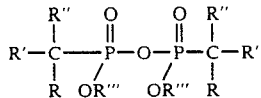

In the above X is F, Cl, Br or I and R, R', R'', R''', R'''' are low value, linear and/or cyclical alkyl groups and/or aryl groups, which can also be substituted and/or hydrogen.

Substituted alkali metal aluminum hydrides, such as for example sodium-bis-2(methoxy-ethoxy)-dihydridoaluminate, have been used successfully as reducing agents.

The solvent used is important principally because the highly pure alkyl and arylphosphines and phosphones can only be removed from this relatively easily by means of distillation if the differences in boiling temperature are correspondingly far from one another. It has been discovered that, for example 1-methylnaphthalin with a boiling point of 242° C., is very well suited as a solvent because it is still fluid even at somewhat lower temperatures—it only hardens at −22° C. Its choice as a solvent is also recommended because although ether and/or ether-containing solvents are likewise fluid in the entire temperature range, even the smallest traces of ethers contaminate the organic phosphines during isolation and lead to disturbances in the epitaxy processes.

During the use of such a solvent, the t-butylphosphine (TBP) for example, can be separated directly out of the reaction apparatus by means of distillation which can be undertaken under very careful conditions. The TBP obtained in accordance with the example accumulates in good yields and has a correspondingly high chromatographic and analytical trace purity.

The following examples illustrate the simple means of preparation in accordance with the invention in greater detail.

EXAMPLE 1

A solution of 130 g (0.74 mol) of t-butylphosphonic acid dichloride in 420 ml of 1-methylnaphthalin is added by dropping, at a temperature between 20° C. and 90°

C., to 344 g (1.7 mol) of sodium-bis-(2-methoxy-ethoxy)-dihydridoaluminate in 200 ml of 1-methylnaphthalin. The product is collected in a cooling precipitator. Additional product can be isolated through the application of a vacuum. The yield is 50 g (75%) of highly pure t-butylphosphine.

EXAMPLE 2

A solution of 99 g (0.57 mol) of 2-butylphosphinic acid dichloride in 200 ml of 1-methylnaphthalin is added by dropping, at a temperature between 20° C. and 90° C., to 344 g (1.70 mol) of sodium-bis-(2-methoxy-ethoxy)-dihydridoaluminate in 200 ml of 1-methylnaphthalin. The product is collected in a cooling precipitator. Additional product can be isolated through the application of a vacuum. The yield is 36 g (71%) of highly pure 2-butylphosphine.

EXAMPLE 3

A solution of 118 g (0.66 mol) of phenylphosphorus dichloride in 300 ml of 1-methylnaphthalin is added by dropping, at a temperature between 20° C. and 90° C., to 168 g (0.84 mol) of sodium-bis-(2-methoxy-ethoxy)-dihydridoaluminate in 400 ml of 1-methylnaphthalin. After the reaction has been completed, the product is isolated through the application of a vacuum. The yield is 49 g (68%) of highly pure phenylphosphine.

I claim:

1. A process for the preparation of alkyl and arylphosphines for gas epitaxy comprising, reducing a compound from the group consisting essentially of alkyl and aryl phosphinic acids, alkyl and arylphosphonic acids, and derivatives of said phosphinic and phosphonic acids with a substituted alkali metal aluminum hydride in a high temperature boiling point hydrocarbon solvent.

2. A process as recited in claim 1, wherein said compound is selected from compounds having at least one functional group selected from alkyl- and arylphosphinic acid groups, alkyl- and arylphosphinic acid groups, dihalogenides of the foregoing acid groups and alkyl and aryl esters of the foregoing acid groups.

3. The process of claim 2, wherein said at least one functional group is an acid dihalogenide group.

4. The process of claim 2, wherein said at least one functional group is an acid ester group.

5. The process of claim 4, wherein each said functional group is completely esterified.

6. The process of claim 2, wherein said starting compound includes two of said functional groups.

7. The process of claim 3, wherein said starting compound includes two of said functional groups.

8. The process of claim 4, wherein said starting compound includes two of said functional groups.

9. The process of claim 5, wherein said starting compound includes two of said functional groups.

10. The process of claim 7, wherein said starting compound includes two phosphonic acid dihalogenide functional groups.

11. The process of claim 8, wherein the said starting compound includes two phosphinic acid ester functional groups.

12. The process of claim 1, wherein the reduction is carried out in a 1-methylnaphtalin in which the salt-like residues from the reaction are soluble.

13. The process of claim 3, wherein the reduction is carried out in a 1-methylnaphtalin in which the salt-like residues from the reaction are soluble.

14. The process of claim 4, wherein the reduction is carried out in a 1-methylnaphtalin in which the salt-like residues from the reaction are soluble.

15. The process of claim 5, wherein the reduction is carried out in a 1-methylnaphtalin in which the salt-like residues from the reaction are soluble.

16. The process of claim 6, wherein the reduction is carried out in a 1-methylnaphtalin in which the salt-like residues from the reaction are soluble.

17. The process of claim 10, wherein the reduction is carried out in a 1-methylnaphtalin in which the salt-like residues from the reaction are soluble.

18. The process of claim 11, wherein the substituted alkali metal aluminum hydride is sodium-bis-(2-methoxy-ethoxy)-dihydridoaluminate.

19. The process of claim 3, wherein the substituted alkali aluminum hydride is sodium-bis-(2-methoxy-ethoxy)-dihydridoaluminate.

20. The process of claim 4, wherein the substituted alkali metal aluminum hydride is sodium-bis-(2-methoxy-ethoxy)-dihydridoaluminate.

21. The process of claim 5, wherein the substituted alkali metal aluminum hydride is sodium-bis-(2-methoxy-ethoxy)-dihydridoaluminate.

22. The process of claim 6, wherein the substituted alkali metal aluminum hydride is sodium-bis-(2-methoxy-ethoxy)-dihydridoaluminate.

23. The process of claim 10, wherein the substituted alkali metal aluminum hydride is sodium-bis-(2-methoxy-ethoxy)-dihydridoaluminate.

* * * * *